United States Patent
Ulmer et al.

(10) Patent No.: US 10,709,821 B2
(45) Date of Patent: Jul. 14, 2020

(54) SEALING STRUCTURE FOR HEART VALVE IMPLANTS

(71) Applicant: BIOTRONIK AG, Buelach (CH)

(72) Inventors: Jens Ulmer, Kuesnacht (CH); Nicolas Degen, Beringen (CH); Urs Huber, Ennetbuegen (CH)

(73) Assignee: BIOTRONIK AG, Buelach (CH)

( * ) Notice: Subject to any disclaimer, the term of this patent is extended or adjusted under 35 U.S.C. 154(b) by 182 days.

(21) Appl. No.: 15/523,927

(22) PCT Filed: Nov. 24, 2015

(86) PCT No.: PCT/EP2015/077464
§ 371 (c)(1),
(2) Date: May 2, 2017

(87) PCT Pub. No.: WO2016/083352
PCT Pub. Date: Jun. 2, 2016

(65) Prior Publication Data
US 2017/0354765 A1 Dec. 14, 2017

Related U.S. Application Data

(60) Provisional application No. 62/083,332, filed on Nov. 24, 2014.

(51) Int. Cl.
*A61F 2/24* (2006.01)
*A61L 31/04* (2006.01)
(Continued)

(52) U.S. Cl.
CPC ...... *A61L 31/042* (2013.01); *A61B 17/12122* (2013.01); *A61F 2/062* (2013.01);
(Continued)

(58) Field of Classification Search
CPC ............ A61F 2/24–2424; A61F 2/2475; A61F 2250/0056; A61F 2250/003;
(Continued)

(56) References Cited

U.S. PATENT DOCUMENTS

| | | |
|---|---|---|
| 4,655,758 A | 4/1987 | Ring et al. |
| 2005/0042250 A1* | 2/2005 | Damien ............ C08B 1/00 424/423 |

(Continued)

OTHER PUBLICATIONS

Mohammadi, H., "Design and simulation of a poly(vinyl alcohol)—bacterial cellulose nanocomposite mechanical aortic heart valve prosthesis", J. Engineering in Medicine Proc. IMechE, vol. 223, Part H, (2009), pp. 697-711.

(Continued)

*Primary Examiner* — Rebecca S Preston
(74) *Attorney, Agent, or Firm* — Greer, Burns & Crain, Ltd; Steven P. Fallon (57) ABSTRACT

A heart valve implant comprising a supporting stent, a heart valve element, and a skirt. The skirt includes or is formed of at least one molded body, wherein the molded body is made of dried treated bacterial cellulose that has a swelling capacity that is greater than untreated bacterial cellulose of the same type.

13 Claims, 4 Drawing Sheets

(51) Int. Cl.

| | |
|---|---|
| A61L 27/20 | (2006.01) |
| A61L 29/04 | (2006.01) |
| A61B 17/12 | (2006.01) |
| A61F 2/06 | (2013.01) |
| A61F 2/07 | (2013.01) |
| A61F 2/08 | (2006.01) |
| A61L 24/00 | (2006.01) |
| A61L 24/08 | (2006.01) |
| A61L 27/50 | (2006.01) |
| A61L 27/54 | (2006.01) |
| A61L 29/16 | (2006.01) |
| A61L 31/10 | (2006.01) |
| A61L 31/16 | (2006.01) |
| A61N 1/362 | (2006.01) |
| A61N 1/375 | (2006.01) |
| A61N 1/39 | (2006.01) |
| B30B 11/00 | (2006.01) |
| C12P 19/04 | (2006.01) |
| D21C 5/00 | (2006.01) |
| A61L 31/14 | (2006.01) |
| A61L 27/36 | (2006.01) |
| A61L 27/56 | (2006.01) |
| A61F 2/915 | (2013.01) |
| A61L 27/58 | (2006.01) |
| A61B 17/00 | (2006.01) |

(52) U.S. Cl.
CPC ............... *A61F 2/07* (2013.01); *A61F 2/08* (2013.01); *A61F 2/2409* (2013.01); *A61F 2/2415* (2013.01); *A61F 2/2418* (2013.01); *A61L 24/0015* (2013.01); *A61L 24/08* (2013.01); *A61L 27/20* (2013.01); *A61L 27/507* (2013.01); *A61L 27/54* (2013.01); *A61L 29/043* (2013.01); *A61L 29/16* (2013.01); *A61L 31/10* (2013.01); *A61L 31/16* (2013.01); *A61N 1/362* (2013.01); *A61N 1/3754* (2013.01); *A61N 1/3956* (2013.01); *B30B 11/005* (2013.01); *C12P 19/04* (2013.01); *D21C 5/00* (2013.01); *A61B 2017/00526* (2013.01); *A61F 2/2412* (2013.01); *A61F 2/915* (2013.01); *A61F 2210/0004* (2013.01); *A61F 2210/0061* (2013.01); *A61F 2220/0016* (2013.01); *A61F 2220/0075* (2013.01); *A61F 2230/0058* (2013.01); *A61F 2240/001* (2013.01); *A61F 2250/0014* (2013.01); *A61F 2250/0023* (2013.01); *A61F 2250/0036* (2013.01); *A61F 2250/0051* (2013.01); *A61F 2250/0069* (2013.01); *A61L 27/3691* (2013.01); *A61L 27/56* (2013.01); *A61L 27/58* (2013.01); *A61L 31/146* (2013.01); *A61L 2300/23* (2013.01); *A61L 2300/41* (2013.01); *A61L 2400/18* (2013.01); *A61L 2430/10* (2013.01); *A61L 2430/20* (2013.01)

(58) Field of Classification Search
CPC ........ A61F 2250/0069–007; A61F 2250/0036; A61F 2210/0061
See application file for complete search history.

(56) References Cited

U.S. PATENT DOCUMENTS

| | | | |
|---|---|---|---|
| 2008/0082164 A1* | 4/2008 | Friedman | A61F 2/2409 623/2.11 |
| 2009/0222085 A1 | 9/2009 | Kumar | |
| 2013/0018458 A1 | 1/2013 | Yohanan et al. | |
| 2013/0331929 A1 | 12/2013 | Mitra et al. | |
| 2015/0051687 A1* | 2/2015 | Dickerhoff | A61F 2/2415 623/1.11 |

OTHER PUBLICATIONS

Galvez, Joelle, et al., "Notification of Transmittal of the International Search Report and the Written Opinion of the International Searching Authority, or the Declaration", Patent Cooperation Treaty Application No. PCT/EP2015/077464, European Patent Office as International Searching Authority, International Search Completed Feb. 15, 2016, International Search Report dated Feb. 23, 2016, (14 pages).

* cited by examiner

SEALING STRUCTURE FOR HEART VALVE IMPLANTS

FIELD OF THE INVENTION

The invention concerns heart valve implants.

BACKGROUND

US 2013/0331929 A1 describes a sealing system that comprises an additional sealing element at the proximal end of a TAVI valve. This contains a hydrogel that is caused to swell by inflowing fluid. The inflow of fluid is allowed only after implantation by a valve that can be controlled from outside.

US 2013/0018458 describes a system consisting of non-swelling materials (here polyethylene terephthalate, PET) that is designed so that in the inflow area of the TAVI valve overhanging materials of the skirt that is normally sutured inside are fixed to the outside of the stent. This is done in such a way that the overhanging material lies loosely in folds against the outside of the stent in the implanted state. This fold formation in the area of the annulus in turn seals existing leakages.

Sealing by swellable hydrogels has negative effects on the durability of these heart valves, since hydrogels generally do not exhibit long-term stability under physiological conditions.

The use of loosely attached PET skirts does not comprise an active element of the seal. Thus, in highly calcified areas of the natural valve annulus leakage flows can still occur, since the PET material cannot conform in a form-fit manner to the calcification.

SUMMARY

A preferred embodiment is a heart valve implant that includes a supporting stent, a heart valve element, and a skirt, wherein the skirt comprises or is formed of at least one molded body, wherein the molded body is made of dried treated bacterial cellulose that has a a swelling capacity that is greater than untreated bacterial cellulose of the same type.

Preferred valves include the storable and swellable molded body that, especially when used for sealing, at least partly reduces the previously mentioned disadvantages, especially leakage flows, that can occur after the implantation of transcatheter heart valves because of so-called paravalvular leaks or leakages.

BRIEF DESCRIPTION OF THE DRAWINGS

Further features and advantages of the invention should be explained below by the description of sample embodiments, especially on the basis of the figures. The figures show FIG. 1(a) On the left, a top view of inventive molded bodies for use as sealing elements to prevent paravalvular leakages when there is a heart valve implant. On the right, in the plane of the section along the stent axis, the molded bodies 1 form a ring; (b) The same views as under (a) with the difference that the molded bodies 1 form two rings.

DETAILED DESCRIPTION OF THE PREFERRED EMBODIMENTS

Heart valves of the invention include a swellable, mechanically stable material with very good biocompatibility and hemocompatibility, the material having an area or areas with greatly different swelling behavior. Thus, the process proposed here can provide a material whose swelling behavior can be especially adjusted in desired subareas for special applications. This material is especially preferred for building a skirt (or skirt area) of an artificial heart valve or a heart valve prosthesis, and is preferably simultaneously used as a sealing element in the heart valve's inflow area.

According to the invention, it is preferable to use bacterial cellulose as a biocompatible material. Bacterial cellulose is an extracellular metabolic product formed by microorganisms, so many of its properties are comparable to those of cellulose of plant origin. However, its purity is significantly higher, since it contains no foreign polymers or other inclusions. The supermolecular structure of bacterial cellulose makes it very hydrophilic and gives it high absorptivity and mechanical strength. For synthesis of cellulose, both gram-negative microorganisms (*Gluconacetobacter* (G.), *Azotobacter, Rhizobium, Pseudomonas, Salmonella, Alcaligenes*) and gram-positive ones (*Sarcina ventriculi*) can be used. The most frequently used of these are *G. xylinus, G. hansenii*, and *G. pasteurianus*, of which *G. xylinus* is especially important. For this invention, the gram-negative aerobic species *Gluconacetobacter xylinus* (formerly also called *Acetobacter xylinum*) is especially important.

A molded body that is made of bacterial cellulose, especially bacterial cellulose from *Gluconacetobacter xylinus*, and that is treated according to this process is advantageously storable, since drying does not make bacterial cellulose brittle, as is the case with conventional drying processes and many other materials. The cellulose can now be processed and stored in the dry state, without the material's positive properties being lost. Surprisingly, it was possible to show that the material's anti-inflammatory properties and good tolerability by the body are preserved just as well as its high mechanical strength.

First, the bacterial cellulose is prepared, preferably in a form suitable for later use. Thus, for example, layers of bacterial cellulose are precipitated, in a manner known in the art, from glucose-containing nutrient solutions inoculated with *Gluconacetobacter xylinus*, and are air-dried. It is just as conceivable to allow a coating of highly purified cellulose fibers to grow directly on a substrate, for example the metallic base body of a stent.

Using suitable culture vessels, it is possible, e.g., to produce layers of bacterial cellulose with different material thickness. To do this, the culture vessel comprises, e.g., a gas-permeable silicone layer of variable thickness that is in contact with the culture solution to be held by the culture vessel. In areas where the silicone layer is of reduced thickness, more air diffuses to the boundary layer between the culture solution and the silicone layer, with the consequence that aerobic bacterial growth increases in this area so that more cellulose is deposited there. In this way it is possible, for example, to produce layers of bacterial cellulose whose thickness ranges from 2 to 10 mm. Thus it is possible to make available a suitable implantation material that can have a thickness greater than that of naturally occurring tissues of human or animal origin which are suitable for the preferred applications as heart valve prosthesis material.

Preparing the necessary molded body from bacterial cellulose might require other preparatory measures, such as purification, pressing, predrying, and cutting and trimming the material. The second step of the inventive process involves subjecting the molded body made of bacterial cellulose required for the respective application to a hot pressing step. The primary goal of the hot pressing step is to remove all or most of the water. To achieve this goal, it is advantageous if this pressing is done sufficiently long and under suitable pressure conditions. The pressure should not be selected to be so strong that the material is mechanically damaged or suffers destruction in the form of cutting or crushing.

Preferably the entire molded body or parts of the molded body are mechanically pressed in the second step at temperatures in the range of 10° C. to 100° C. and pressed in the range of 0.0005 to 1.5 MPa, more preferably 0.01 to 1 MPa for 10-200 min. Hereby the swelling capacity of the cellulose is reduced and can thus be adjusted to meet desired requirements. Also the mechanical stability of the material is increased.

In the third step, the pressed molded body is preferably treated with the C1-C3 alcohol/water mixture (for example methanol, ethanol, 1-propanol, and 2-propanol) and glycerol, especially a glycerol-containing isopropanol/water solution, this treatment especially being washing or incubation in the solution.

The solution preferably contains between 20 weight % and 50 weight % of glycerol, the rest being the C1-C3 alcohol/water mixture.

The ratio of C1-C3 alcohol to water in the C1-C3 alcohol/water mixture is preferably between 90 to 10 and 70 to 30. Especially preferred is a C1-C3 alcohol/water mixture formed of 80 weight % C1-C3 alcohol, especially isopropanol, and 20 weight % water.

It is preferable for the proportion of water in the incubation solution consisting of glycerol and a C1-C3 alcohol/water mixture not to exceed 20 weight %. The solution can contain other components, however it is preferably limited to the mentioned three components. Usually, the time period of the incubation in the solution is, e.g., 0.5 to 24 h, however preferably 12 hours.

Then, the molded body treated with the solution is preferably dried. This can be done by suitable processes. In one embodiment, the drying can be done in the air (1 to 2 days). Air drying at room temperature (typically between 20 and 25° C.) removes the alcohol that is present and most of the water from the cellulose. The drying can also be done under vacuum or in a climate-controlled cabinet. After drying, the cellulose regularly still has a glycerol content between 0.1 and 10 weight %, with a reference value of 1.5 weight %. The presence of water cannot be excluded, since glycerol is hygroscopic.

An especially preferred embodiment of the inventive process provides that in the second step ii) of the process the temperature is preferably in the range from 80° C. to 100° C. and the pressure is preferably in the range from 1.5 MPa to 2 MPa. In a different embodiment the pressure can be preferably in the range from 1.0 to 10 kPa and more preferably 1.5 kPa to 2 kPa at a temperature range of 80° C. to 100° C.

The bacterial cellulose treated according to the inventive process is advantageously storable, the desired anti-inflammatory properties and compatibility of the material being preserved.

It has proved advantageous that the inventive process can also be used to change the swelling capacity of the cellulose in a selective manner. Here the invention is based especially on the knowledge that dried bacterial cellulose, especially bacterial cellulose of *Gluconacetobacter xylinus*, can, contrary to prevailing opinion, be completely or almost completely rehydrated using the present process or rather special drying process, or the water absorbency can be even further increased by the drying process in parts or portions, while the second step ii) can specially limit the swelling behavior of other subareas, thus allowing the water absorbency to be adjusted.

Therefore, the swelling capacity of the entire molded body or parts of the molded body can be adjusted by the mechanical pressing in step ii) to meet the existing requirements for the respective application. In other words, the swelling capacity of different areas of one and the same molded body can vary independently of one another.

Accordingly, another aspect of the invention relates to a storable and possibly swellable molded body made of bacterial cellulose as described in claim 3 that was produced by the previously portrayed inventive process.

In the context of the invention, a molded body is understood to be any sort of a physical piece molded in any way. In the simplest case, this can be a flat-shaped body perceived to be two-dimensional (with relatively small thickness compared with its width and length) or an almost two-dimensional planar piece (similar to a strip of fabric). In the same way it is understood to mean more complicated three-dimensional shapes such as cylindrical tube sections, all the way to more complex shapes such as, for example, heart valves.

Another aspect of the invention relates to a heart valve implant comprising a supporting stent, a heart valve element, and a skirt, the skirt having at least one inventive molded body, or comprising one, or being formed of at least one molded body (1).

A preferred embodiment of the inventive heart valve implant provides that the at least one molded body has at least one area that has lower swelling capacity than an adjacent area of the molded body, preferably due to treatment with the mechanical pressing described in step ii). It is also conceivable to lower the swelling capacity of the entire molded body defined by the aforementioned pressing.

A preferred embodiment of the inventive heart valve implant also provides that the skirt comprises an area for sealing paravalvular leakages. Here paravalvular leakages mean leakages in which blood flows past the implant, between the surrounding vessel wall or the native heart valve and the implant.

A preferred embodiment of the inventive heart valve implant also provides that the skirt is attached in the luminal and/or abluminal area of the supporting stent. Here the luminal area of the supporting stent comprises, in particular, an inner surface of the stent, while the abluminal area of the supporting stent comprises an outer surface of the supporting stent facing away from this inner surface. This skirt can have areas or subareas that do not consist of bacterial cellulose as described here, but rather of other materials. However it is just as conceivable for the skirt to consist of bacterial cellulose as described herein. In an embodiment in which areas of the skirt consist of materials other than bacterial cellulose as described here, then the skirt comprises at least one molded part made of bacterial cellulose as described herein that has been treated according to the process proposed here.

A preferred embodiment of the inventive heart valve implant also provides that the skirt runs in the luminal and abluminal area of the supporting stent and furthermore that the skirt has reduced swelling capacity in the luminal area, preferably due to treatment by the mechanical pressing described in step ii), at least parts of the skirt furthermore having a higher swelling capacity in the abluminal area.

A preferred embodiment of the inventive heart valve implant also provides that the skirt is attached on the luminal side of the supporting stent and that at least one molded body, preferably multiple molded bodies, are attached, preferably sutured in, between the stent struts and the skirt attached on the luminal side. This at least one molded body is made of the bacterial cellulose proposed here, and has areas with increased swelling behavior. The at least one molded body or multiple molded bodies that have increased swelling behavior is/are preferably arranged between the supporting stent and a skirt made of non-swellable material, the increase in volume of the swelling molded body being directed radially outward, causing swelling between the stent struts. This skirt running in the luminal area can be made of bacterial cellulose as described here or also of other suitable, especially non-swellable materials such as polymers or other artificial materials or biological tissue, especially of animal origin, such as pericardium or lung, stomach, or intestinal tissue. In a preferred embodiment, the at least one molded body is attached between a node of the stent framework and the skirt running in the luminal area. In another embodiment, the multiple molded bodies are arranged in such a way that molded parts attached next to one another border one another so as to form preferably at least one closed ring in the peripheral direction of the skirt. Embodiments involving luminal arrangement in the stent framework have the advantage, in addition to effective sealing of leakages, that complication-free re-sheathing is possible with them.

A preferred embodiment of the inventive heart valve implant also provides that the skirt is attached in the luminal area to an end of the supporting stent close to the heart valve or in the inflow area, and that the molded parts form at least two closed rings in the longitudinal direction. It is advantageous for the at least one molded body to be sutured between the skirt and the stent framework, preferably to the stent struts and also to the nodes of the stent framework.

A preferred embodiment of the inventive heart valve implant also provides that at least some of the borders or edges of the aforementioned molded body run on the stent struts of the supporting stent.

A preferred embodiment of the inventive heart valve implant also provides that the skirt is attached in the luminal area of the supporting stent and that the areas that run under the stent struts of the supporting stent have reduced swelling capacity, preferably due to treatment with the mechanical pressing described in step ii).

A preferred embodiment of the inventive heart valve implant also provides that the skirt runs in the luminal and abluminal area of the supporting stent and is alternately braided around the stent struts of the supporting stent in the form of at least one band running around the circumference, and that the areas that run on the luminal side under the stent struts of the supporting stent have reduced swelling capacity, preferably due to treatment with the mechanical pressing described in step ii).

A preferred embodiment of the inventive heart valve implant also provides that the heart valve element has at least one heart valve leaflet made of an inventive molded body.

A preferred embodiment of the inventive heart valve implant also provides that the heart valve element has three heart valve leaflets made of one inventive molded body, or each made of one inventive molded body.

Example 1

Figure 1A:
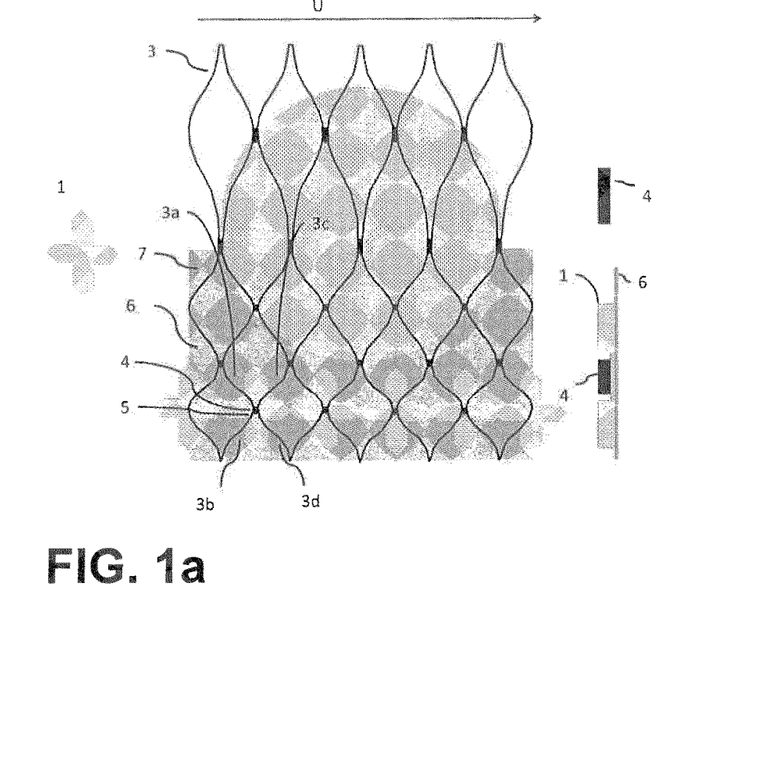
Figure 1B:
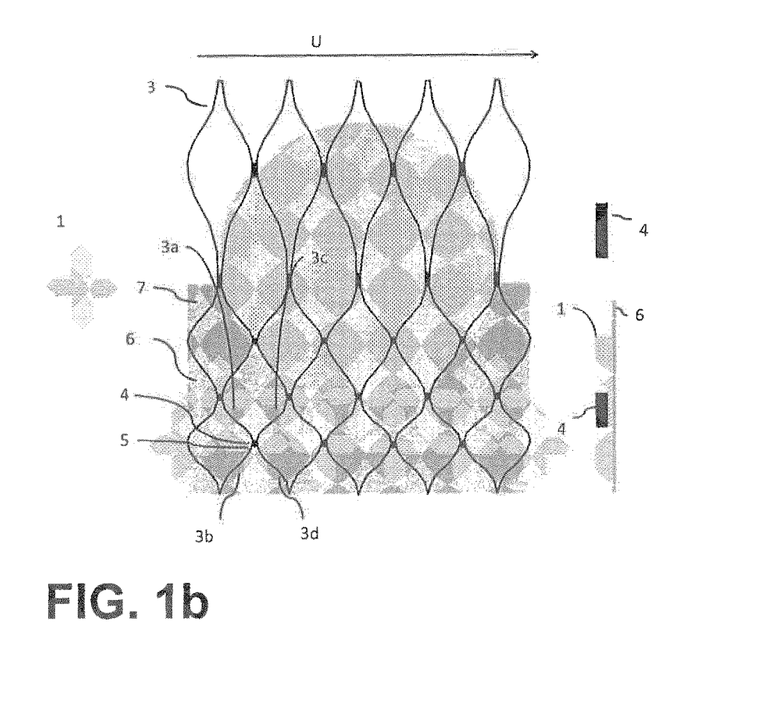

Native microbial cellulose is incubated overnight in a 20-30 weight % alcoholic glycerol solution (e.g., 30 weight % glycerol, 56 weight % isopropanol, 14 weight % water) and then air-dried at room temperature. Using a cutting device, small pieces 1 of swellable cellulose are separated, as shown in FIG. 1, and sutured between the stent struts 3a, 3b, 3c, 3d and the skirt area (skirt) 6 running around supporting stent 3 in the peripheral direction U. The individual stent struts 3a, 3b, 3c, 3d are arranged in such a way that every four such adjacent struts 3a, 3b, 3c, 3d of the supporting stent 3 delimit an opening, in particular a rhombus-shaped one, that is also called rhombus for short. Every four of these struts 3a, 3b, 3c, 3d are always connected with one another through a node 4, in particular they are formed to one another in one piece. An upper or lower half of such a rhombus is called an upper or lower semi-rhombus.

The suture points 5 are attached in the nodes 4 of the rhombi, which are in the lower third of supporting stent 3. One element 1 is attached to each node 4 of the lowermost rhombus plane so that this element 1 is fixed between node 4 and skirt 6. This element 1 has, in the area of the node, reduced swelling capability introduced by the process presented herein produces by means of hot pressing, and in all other areas this element 1 has increased swelling capability. FIGS. 1a and 1b show two embodiments regarding this in which the elements 1 are attached to nodes 5 so that the elements 1 come to lie against one another. If sufficiently many elements 1 are fastened to the supporting stent 3, the elements 1 form a ring running around the stent framework (FIG. 1a), or even two rings, as shown in FIG. 1b.

Example 2

Microbial cellulose (here also called bacterial cellulose, in the example shown herein with a thickness of around 6 mm) is partially dried using a hot press, which reduces the thickness of the dried area by a factor of 50 in comparison with the undried area. After partial drying, the microbial cellulose is incubated overnight in a 20-30 weight % alcoholic glycerol solution (e.g., 30 weight % glycerol, 56 weight % isopropanol, 14 weight % water) and then air-dried at room temperature. In the non-hot pressed area, the cellulose treated in this way has a layer thickness of 0.5 mm to 0.7 mm and in the hot-pressed area it has a layer thickness of less than 0.1 mm. When remoistened, the layer thickness increases to 4.0 mm to 5 mm in the non-hot pressed area. By contrast, the cellulose in the hot pressed area only swells up to a layer thickness of 0.1 mm to 0.2 mm.

Example 3

Figure 2:
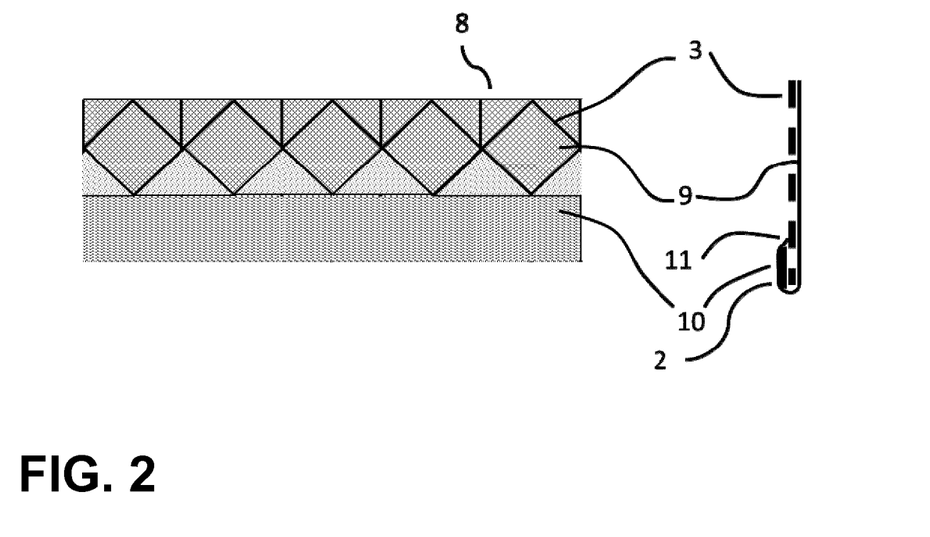
FIG. 2 a skirt suitable for a balloon-expandable stent framework. On the left in unrolled top view. On the right in the section plane along the stent axis.
Figure 3:
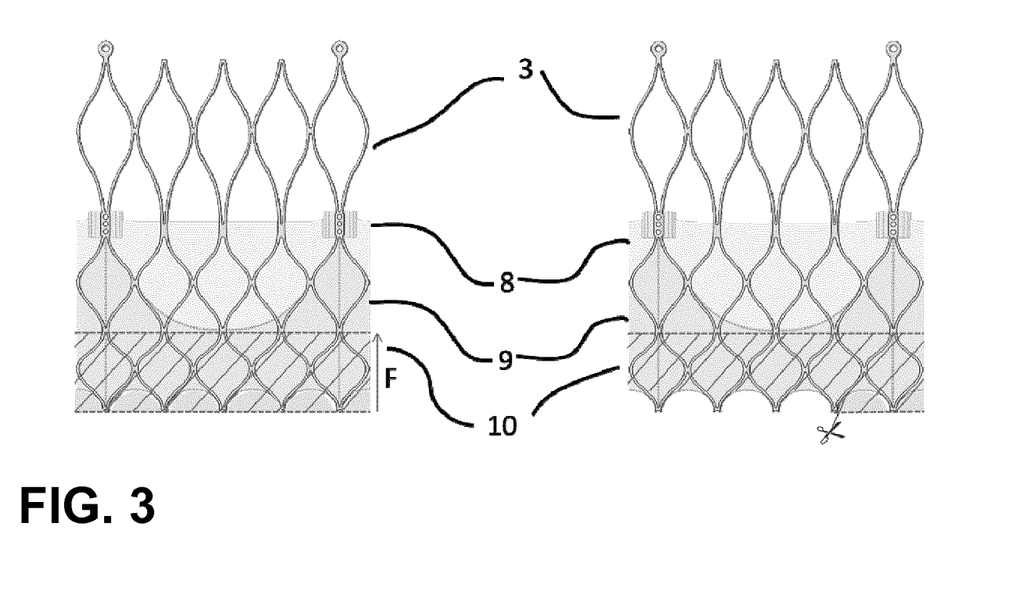
FIG. 3 a skirt suitable for a balloon-expandable stent framework. On the left in top view after the skirt is folded down. On the right, top view after skirt parts have been cut away at the lower end of the prosthesis.

Using a cutting device, e.g., correspondingly matching parts are cut out of the non-woven cellulose (1) treated in Example 2 to build a skirt or a skirt area. After that, a skirt can be formed, as shown in the embodiments of FIGS. 2 and 3. The lower third of it consists of non-hot pressed cellulose 2 that has an increased swelling capability. The non-woven cellulose for the skirt area of a prosthesis is oriented so that the non-hot pressed area comes to lie downward, toward the operator. An operator can be a certified, experienced, and well-trained specialist in the area of suturing heart valve heart valve prostheses. The lower area is folded up once (labeled in FIG. 3 by the arrow and F), so that the lowermost cell row of the inflow area is double covered. Then, the three skirt parts are cut out of the cellulose, the gaps between the struts not being cut out in the inflow area. The folded part is sutured to the skirt, preferably using Armenian suturing technique, to prevent the possibility that blood will sneak through. After that, three skirt parts with 3 leaflets are sutured together. Then, the three valve parts are sutured into a complete valve. After the valve inspection, the complete valve is sutured into the stent. Thus, in this embodiment all the valve material, together with the area especially capable of swelling, lies inside the stent. This embodiment is especially advantageous since it is possible to carry out re-sheathing without complications. At the end, a small pair of curved scissors is used to trim the gaps between the struts in the inflow area (FIG. 3, left side, bottom).

Example 4

Microbial cellulose cut into strips or threads is woven into the stent structure. When this is done, the honeycomb structure of the stent is exploited by always passing the thread/strip once over and once under the strut.

The parts of the thread/strip that lie beneath the strut (between the stent and the inner skirt) can be modified by hot pressing so that they do not swell, or do so only very little. Thus, the inside diameter of the valve does not shrink, or shrinks only very little.

This processing prevents longitudinal slippage of the resulting structure.

The initial and final thread(s)/strip(s) can either be tied together, and thus form a loop around a strut, or be tied directly to a strut. In both cases a reduction of suture points is achieved, in direct comparison with the flat skirt.

Figure 4:
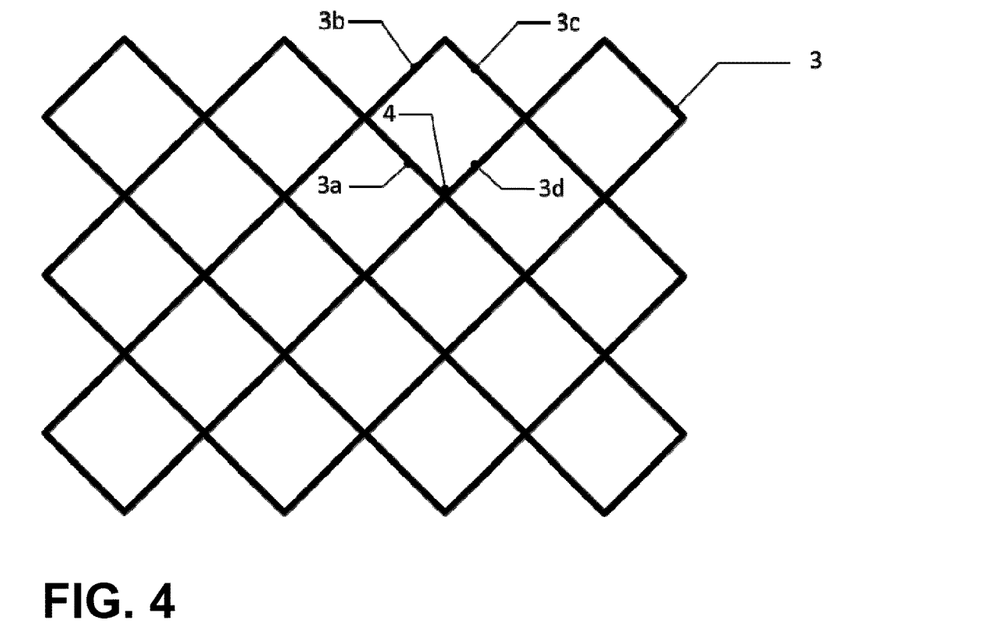
FIG. 4 a simplified representation of the stent framework with stent struts and nodes.

Two embodiments are considered in detail as examples of this. FIG. 4 first shows, as a starting point, a stent with stent framework 3 and stent struts 3a, 3b, 3c, and 3d, which form a rhombus. At one vertex of the rhombus there is a node 4.

Figure 5:
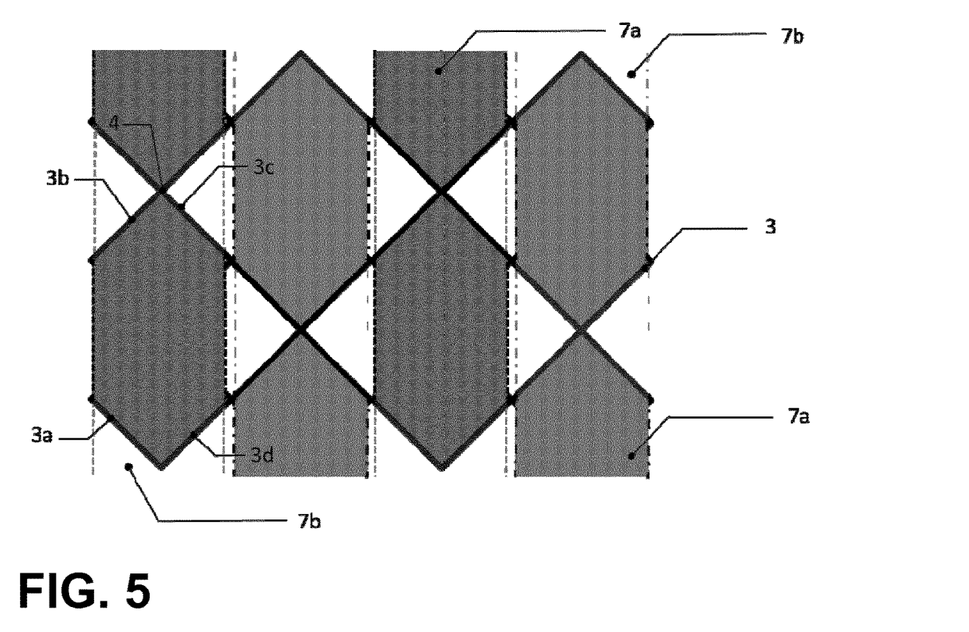
FIG. 5 a view of the skirt area, in which strips of cellulose run above and below the stent struts.
Figure 7:
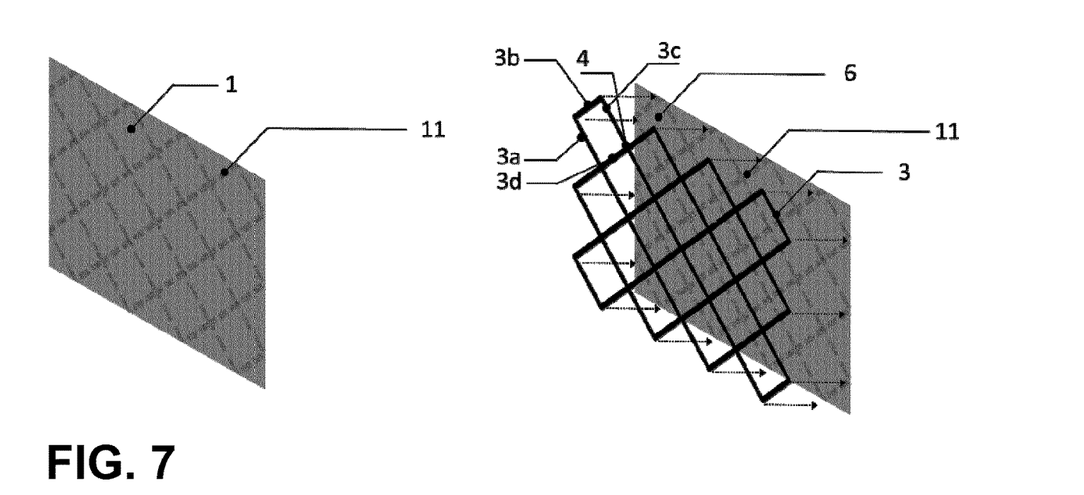
FIG. 7 a skirt for a balloon-expandable stent framework. On the left, a piece of cellulose is shown in which lattice-shaped areas have been made with reduced swelling capacity. On the right, the piece of cellulose that is shown alone on the left with a matching stent framework having dimensions such that the stent struts come to lie over the areas with reduced swelling behavior.

Starting from such a stent, FIG. 5 shows an embodiment in which strips of the inventive cellulose are woven into the stent structure. In this embodiment, the strips are woven so that they pass over and under the nodes 4. This produces surfaces 7a that are over stent struts 3a, 3b, 3c, and 3d and nodes 4, and surfaces 7b, that lie under them. As is also shown in FIG. 7, this cellulose can be pretreated so that areas that lie under stent struts 3a, 3b, 3c, and 3d and nodes 4 have lower swelling behavior. The cellulose strips can preferably also be arranged so that the edges of the strips overlap on a narrow width, preventing a simple flow (indicated by broken lines).

Figure 6:
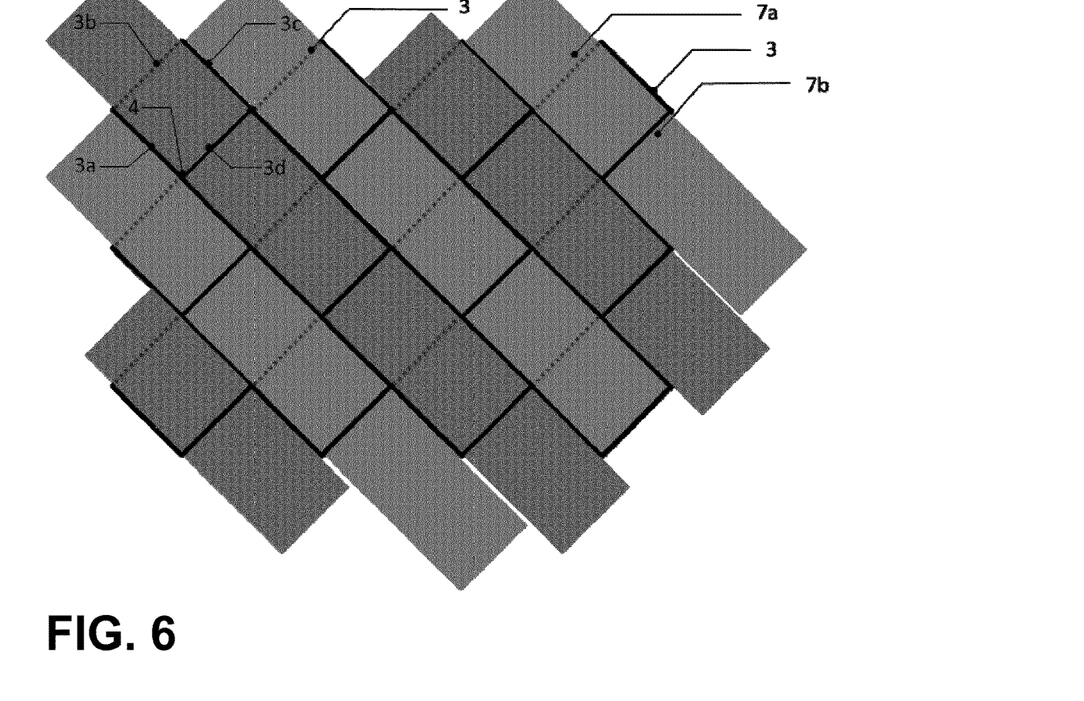
FIG. 6 another view of the skirt area, in which strips of cellulose run above and below the stent struts.

FIG. 6 shows another embodiment in which strips of the inventive cellulose are woven into the stent structure. In this embodiment, the strips do not, as in FIG. 5, pass under and over the nodes 4, but rather over and under stent struts lying in a row, preferably directly opposite stent struts 3a and 3c and 3b and 3d in alternation. In FIG. 6, stent struts that lie under the cellulose are shown as broken lines, while stent struts that lie above the cellulose are shown as a thick, solid line. FIG. 6 also shows areas that lie over the stent structure (7a) and that lie under the stent structure (7b). Interweaving the cellulose into the stent structure produces a steady alternation between areas 7a and 7b.

Example 5

A planar piece of microbial cellulose is fastened to the outside of the stent structure. This renders it possible to tell whether the surface is sutured with the stent at a few suspension points, or at many points along the struts (quilt principle).

Here it is crucial that the microbial cellulose can be modified by hot pressing in the areas of the sutures so that its swelling characteristics are clearly decreased there. This characteristic can clearly reduce the load on the sutures, without losing the sealing characteristic caused by swelling in the decisive regions radially surrounding the stent body.

For further illustration, see the example in FIG. 7. FIG. 7 first shows, on the left, a piece of cellulose 1 in which lattice-shaped areas with reduced swelling capacity 11 have been made. These areas 11 can be in the area of sutures, but also under sutures and the stent struts, for example, as shown on the right. Here a piece of cellulose is shown, such as is shown alone on the left, with a matching stent framework 3 that has dimensions such that stent struts 3a, 3b, 3c, and 3d and nodes 4 come to lie over the areas with reduced swelling behavior 11, and thus do not exert excessive pressure on the sutures or the stent framework 3, and such that they also contribute to good sealing due to the increased swelling behavior between the stent struts.

Example 6

For a balloon-expandable valve framework 8, it is possible to use non-woven cellulose that has been hot-pressed in parts. This involves designing the nonwoven fabric so that it has an inside skirt area 9 and an outside 10 skirt area, such as have already been shown as examples in FIGS. 2 and 3. This inside skirt area 9 is hot-pressed and accordingly non-swellable. This skirt area is firmly sutured from inside with the balloon-expandable stent frame 3. The outside skirt area 10 is turned around the inflow area I and sutured to frame 3 from outside. This outside skirt area 10 is made so that the cellulose in the area of the suture points 11 is non-swellable.

The invention claimed is:

1. A heart valve implant comprising a supporting stent, a heart valve element, and a skirt, wherein the skirt comprises or is formed of at least one molded body, wherein the at least one molded body is made of dried treated bacterial cellulose that has a swelling capacity that is greater than untreated bacterial cellulose of the same type, wherein a selected one of the at least one molded body has at least one area that has a lower swelling capacity than an adjacent area of the same selected one of the at least one molded body.

2. The heart valve implant according to claim 1, wherein the skirt comprises an area for sealing paravalvular leakages.

3. The heart valve implant according to claim 1, wherein the skirt is attached in the luminal and/or abluminal area of the supporting stent.

4. The heart valve implant according to claim 3, wherein the skirt runs in the luminal and abluminal area of the supporting stent, the skirt having reduced swelling capacity in the luminal area and higher swelling capacity in at least parts of the abluminal area.

5. The heart valve implant according to claim 3, wherein the skirt is attached in the luminal area and comprises multiple molded bodies, the multiple molded bodies being attached between the stent framework and the skirt running in the luminal area.

6. The heart valve implant according to claim 5, wherein the multiple molded bodies are arranged in such a way that molded parts attached next to one another border one another so as to form at least one closed ring in the peripheral direction of the skirt.

7. The heart valve implant according to claim 3, wherein the skirt is attached in the abluminal area of the supporting stent, and wherein the areas of the skirt that are over stent struts and nodes of the supporting stent have reduced swelling capacity.

8. The heart valve implant according to claim 3, wherein the skirt runs in the luminal and abluminal area of the supporting stent and is alternately braided around stent struts of the supporting stent in the form of at least one band running around the circumference, and wherein the areas of the skirt that run on the luminal side under the stent struts of the supporting stent have reduced swelling capacity.

9. The heart valve implant according to claim 1, wherein the borders of the at least one molded body run at least partly on stent struts of the supporting stent.

10. The heart valve implant according to claim 1, wherein the heart valve element comprises at least one heart valve leaflet formed as part of the at least one molded body.

11. The heart valve implant according to claim 10, wherein the heart valve element comprises three heart valve leaflets formed as part of the at least one molded body.

12. The heart valve implant of claim 1, wherein the dried bacterial cellulose is from one of the following bacteria: *Gluconacetobacter* (*G.*), *Azotobacter, Rhizobium, Pseudomonas, Salmonella, Alcaligenes, G. xylinus, G. hansenii, G. pasteurianus*, and *Gluconacetobacter xylinus* (also called *Acetobacter xylinum*).

13. The heart valve implant of claim 1, wherein the dried bacterial cellulose is from *Gluconacetobacter xylinus*.

\* \* \* \* \*